(12) United States Patent
Reidt et al.

(10) Patent No.: US 6,482,284 B1
(45) Date of Patent: Nov. 19, 2002

(54) METHOD OF MAKING A DENTAL MILL BLANK AND SUPPORT STUB ASSEMBLY

(75) Inventors: Dean K. Reidt, Cottage Grove, MN (US); Darin J. Meyertholen, Woodbury, MN (US); John R. Cheney, Hugo, MN (US); Robert M. Biegler, Woodbury, MN (US); Robert E. Brunsell, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 272 days.

(21) Appl. No.: 09/653,230

(22) Filed: Aug. 31, 2000

(51) Int. Cl.[7] .................................................. B31F 1/00
(52) U.S. Cl. ........................... 156/200; 264/16; 264/19; 264/328.7; 264/328.9; 156/294
(58) Field of Search ........................... 264/328.7, 328.9, 264/16, 19, 225, 161; 156/293, 294, 153, 154, 245; 451/389, 397, 398

(56) References Cited

U.S. PATENT DOCUMENTS

| | | | |
|---|---|---|---|
| 2,186,468 A | * | 1/1940 | Schwartz ..................... 264/19 |
| 4,411,626 A | | 10/1983 | Becker et al. |
| 4,478,580 A | | 10/1984 | Barrut |
| 4,503,169 A | | 3/1985 | Randklev |
| 4,575,805 A | | 3/1986 | Moermann et al. |
| 4,615,678 A | | 10/1986 | Moermann et al. |
| 4,663,720 A | | 5/1987 | Duret et al. |
| 4,742,464 A | | 5/1988 | Duret et al. |
| 4,766,704 A | | 8/1988 | Brandestini et al. |
| 4,837,732 A | | 6/1989 | Brandestini et al. |
| 4,842,454 A | | 6/1989 | Gustavsson et al. |
| 4,954,080 A | | 9/1990 | Kelly et al. |
| 4,970,032 A | | 11/1990 | Rotsaert |
| 5,092,022 A | | 3/1992 | Duret |
| 5,106,303 A | | 4/1992 | Oden et al. |
| 5,135,393 A | | 8/1992 | Eidenbenz et al. |
| 5,151,044 A | | 9/1992 | Rotsaert |
| 5,224,049 A | | 6/1993 | Mushabac |
| 5,342,696 A | | 8/1994 | Eidenbenz et al. |
| 5,378,154 A | | 1/1995 | Van Der Zel |
| 5,383,752 A | | 1/1995 | Rheinberger et al. |
| 5,417,572 A | | 5/1995 | Kawai et al. |
| 5,587,912 A | | 12/1996 | Andersson et al. |
| 5,691,905 A | | 11/1997 | Dehoff et al. |
| 5,788,498 A | | 8/1998 | Wohlwend |
| 5,813,859 A | | 9/1998 | Hajjar et al. |
| 5,851,115 A | | 12/1998 | Carlsson et al. |
| 5,880,962 A | | 3/1999 | Andersson et al. |
| 5,910,273 A | | 6/1999 | Thiel et al. |

FOREIGN PATENT DOCUMENTS

| | | |
|---|---|---|
| DE | 196 12 699 | 7/1997 |
| DE | 197 33 161 | 2/1999 |
| EP | 0 455 854 | 11/1991 |
| EP | 0 850 601 | 12/1997 |
| EP | 634 150 | 2/1999 |
| WO | WO 96/37163 | 11/1996 |
| WO | WO 99/62422 | 12/1999 |
| WO | WO 00/40206 | 7/2000 |

OTHER PUBLICATIONS

U.S. patent application Ser. No. 09/168,051 filed Oct. 7, 1998, Bretscher et al.

(List continued on next page.)

*Primary Examiner*—Michael W. Ball
*Assistant Examiner*—Barbara J Musser
(74) *Attorney, Agent, or Firm*—James D. Christoff

(57) ABSTRACT

A mill blank assembly for making a dental prosthesis includes a milling section and a support section. The support section is adapted to fit in a chuck or collet of a milling machine. One of the milling section and the support section includes a projection that extends into a recess of the other, in order to enhance the strength of the bond between the milling section and the support section. As a result, the completed assembly is less likely to fracture or become disassembled during the milling process.

15 Claims, 2 Drawing Sheets

OTHER PUBLICATIONS

U.S. patent application Ser. No. 09/227,230 filed Jan. 8, 1999, Rusin et al.

U.S. patent application Ser. No. 09/383,560 filed Aug. 26, 1999, Rusin et al.

U.S. patent application Ser. No. 09/428,830 filed Oct. 28, 2000, Windisch et al.

U.S. patent application Ser. No. 09/428,937 filed Oct. 28, 2000, Zhang et al.

U.S. patent application Ser. No. 09/429,185 filed Oct. 28, 2000, Zhang et al.

JADA, vol. 128, Mar. 1997, A Review of All–Ceramic Restorations, p. 297–307.

Girrbach Dental–Systeme, diGident CadCam Frei–Form Wahl–Frei.

* cited by examiner

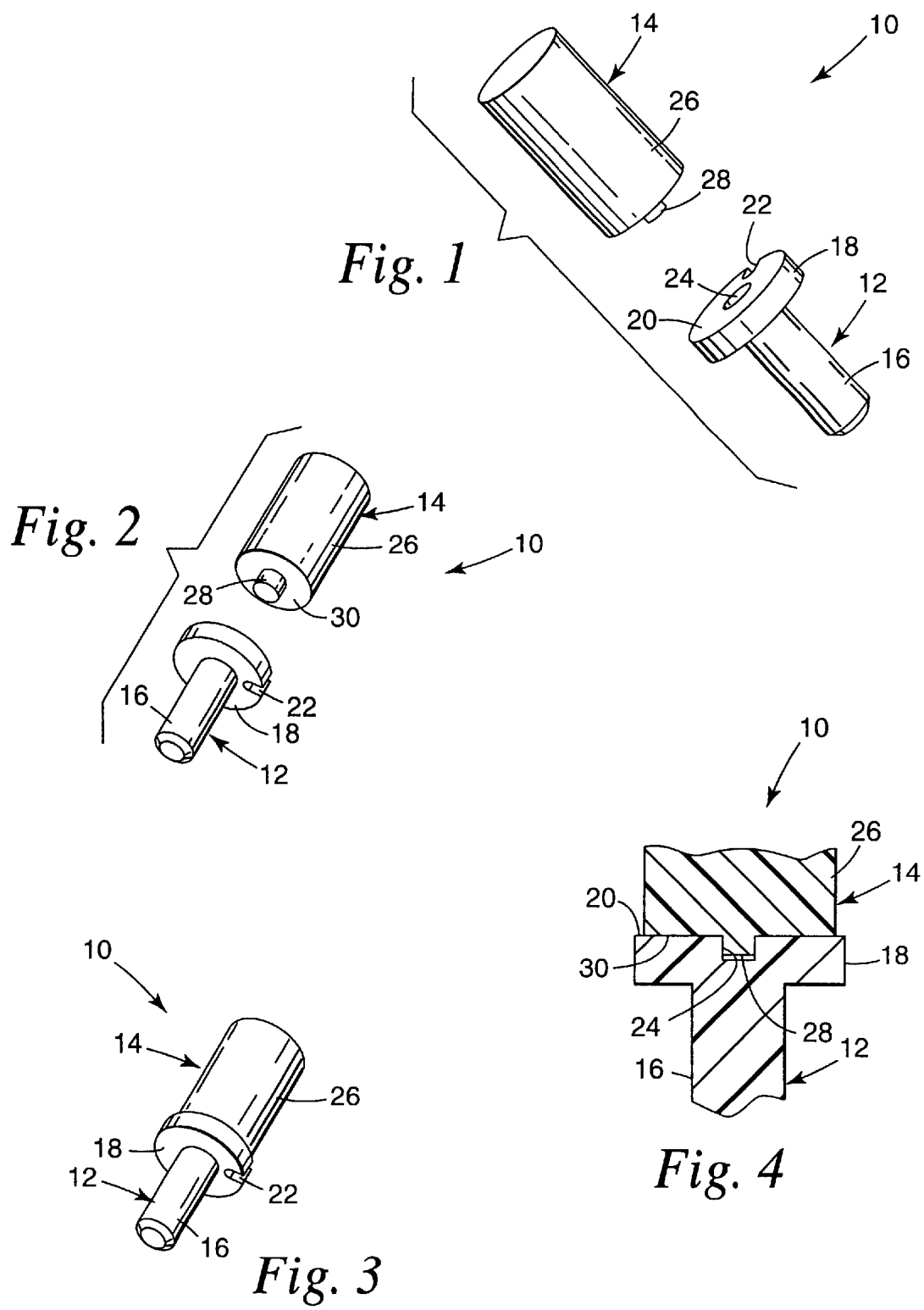

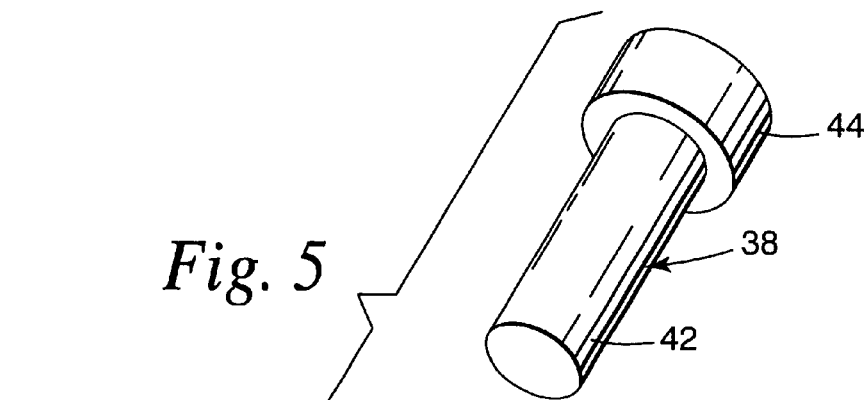
Fig. 5
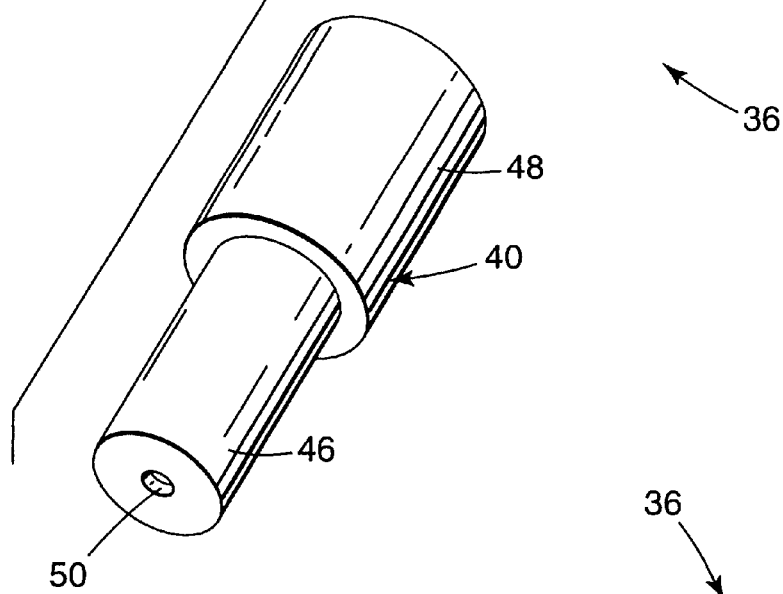
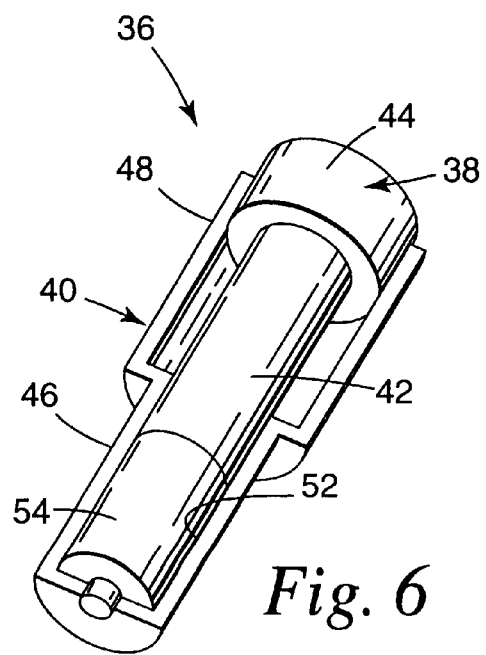
Fig. 6

METHOD OF MAKING A DENTAL MILL BLANK AND SUPPORT STUB ASSEMBLY

BACKGROUND OF THE INVENTION

1. Field of the Invention

This invention broadly relates to a mill blank assembly used in the field of dentistry to create an inlay, onlay, crown, veneer, coping, bridge, bridge framework, implant, implant abutment or other restoration or restoration component. More specifically, the present invention is directed to a mill blank assembly that is especially adapted for use with computer-aided design and machining processes to create a dental prosthesis.

2. Description of the Related Art

A variety of dental procedures are known for replacing or repairing damaged, weakened or missing tooth structures. For example, a dental prosthesis commonly known as a filling is often used to fill cavities in teeth caused by tooth decay or caries. Somewhat larger prosthetics also used to fill cavities are known as inlays and onlays. Fillings, inlays and onlays may also be utilized to restore the shape of teeth that have been chipped or broken.

Other types of dental prosthetics include bridges, full crowns and partial crowns. Typically, these prosthetics are much larger than fillings and as a result are often more visible in the oral cavity. Full and partial crowns may be supported by remaining portions of the original tooth structure and/or by a post extending toward the bony region of the jaw. Bridges, on the other hand, are structures that connect to adjacent tooth structure and provide an artificial tooth or tooth crown to replace corresponding, missing structure.

In the past, fillings and some inlays and onlays were often made of a silver-colored metal alloy known as amalgam due to its relatively long life and relatively low cost. Another advantage offered by amalgam is that it allows a dental practitioner to fit and fabricate the restoration during a single session with a patient. Unfortunately, amalgam is not considered aesthetic since its silver color sharply contrasts to the appearance of natural teeth in the oral cavity.

Another material used for dental prosthetics, and particularly for larger inlays and fillings, is gold. However, like amalgam, the color of gold sharply contrasts with the appearance of natural teeth and is highly visible in the oral cavity. In addition, gold is relatively expensive in comparison to other dental materials.

As a consequence, many dental practitioners are increasingly turning to ceramic or polymer-ceramic composite materials for use to make dental prosthetics. Dental ceramic materials and dental polymer-ceramic composite materials can provide an appearance that closely matches the appearance of natural teeth. Such materials are also available in various color shades so that the practitioner can select a color that closely matches the color of adjacent tooth structure.

Dental polymer-ceramic composite materials for use as restoratives are available from various manufacturers in paste-type form. Such materials are often supplied in capsules that are releasably received in a receptacle of a hand-held dispenser. The dispenser typically includes a lever that, when depressed, extrudes a quantity of the material from the capsule and directly onto the tooth structure. The material includes a polymerization initiator that serves to harden the material once it has been placed on the tooth structure and shaped by the practitioner to resemble natural tooth structure.

A variety of techniques may be employed to help shape the unhardened restorative paste to a desired configuration once dispensed onto the patient's tooth structure. For example, if the material is used to fill a relatively small cavity, the material can be dispensed directly into the cavity and then shaped by hand. A hand instrument such as a dental pick is used to help pack the material in the cavity and to blend the external surface of the paste with adjacent, external portions of the patient's tooth. As another example, if a portion of one or more sides of a tooth is to be restored, the practitioner may elect to use a matrix band or sectional matrix band next to the tooth structure to help hold the material in place while it hardens. The matrix band or sectional matrix band serves as a formwork, similar to formwork used in concrete, to help hold the material in place and also to help define an outer surface of the composite material while it hardens.

However, larger prosthetics are often fabricated outside of the oral cavity and then placed in the patient's oral cavity once completed. For these types of prosthetics, an impression is often taken of the patient's tooth structure of interest along with adjacent regions of the gingiva, using an elastomeric impression material that provides a negative physical image of the tooth structure and gingival region. Next, a cast positive model is made by pouring a quantity of plaster of Paris into the impression and allowing the plaster of Paris to harden. The resulting plaster of Paris or "stone" model is then used in the laboratory to make a prosthetic that is ultimately transferred to the patient's oral cavity.

The laboratory procedure for making the prosthetic may be somewhat involved, depending on the type of prosthetic that is needed. In one method, for example, a wax replica of the desired crown is built on the stone model. The wax replica is then embedded in a refractory investment material and fired to create another negative physical image of the oral structure of interest. Porcelain is then forced into the investment material under pressure and heat in order to make the crown.

However, a number of disadvantages arise when the foregoing procedure is followed to make a crown. In such a procedure, the patient typically travels to the practitioner's office two times: a first time to enable an impression to be taken, and a second time a few days later after the stone model has been made and the crown has been fabricated in the dental laboratory. Moreover, if the completed crown must be returned to the laboratory because its shape, fit or appearance is not satisfactory, the patient is often then required to return to the dental office for a third visit. In many dental practices, the crown is not made in a laboratory that is part of the office but is instead sent to a central laboratory in another area of the town or region.

Furthermore, the fabrication of custom dental crowns and other prosthetics by hand from stone models is an art that involves a high degree of skill and craftsmanship, as well as intensive labor. Moreover, prosthetics that are placed in the anterior regions of the patient's oral cavity are often highly visible. It is widely considered difficult to make a porcelain prosthetic that exactly matches the translucency and color of natural teeth.

Recently, increased interest has been directed toward the use of computer automated machinery for fabricating dental prosthetics, using far less labor than prior methods such as the method for making a crown described above. For example, several systems are known for collecting a set of electronic data that is representative of the patient's tooth structure of interest. The data is then used by an automated mechanical milling machine (such as computer-aided milling machine) to fabricate a prosthetic that, when completed, closely matches the shape of natural tooth structure.

Examples of computer-aided milling machines used in the field of dentistry include the CEREC 2™ and CEREC 3™ machines available from Sirona Dental Systems of Bensheim, Germany, the VITA CELAY™ machine from Vita Zahn Fabrik of Bad Sackingen, Germany, PROCAM™ from Intra-Tech Dental Products, of Dallas, Tex. and PROCERA ALL CERAM™ from Nobel Biocare USA of Westmont, Ill. U.S. Pat. Nos. 4,837,732, 4,776,704 and 4,575,805, as well as PCT patent application No. WO 96/37163 also disclose systems for making dental prosthetics using computer-aided milling machines.

The fabrication of a dental prosthesis using a computer-aided machining system typically involves the use of a "mill blank", a block of material from which the prosthetic is cut. Dental mill blocks are often made of a ceramic material. Commercially available dental mill blanks include VITA CELAY™ porcelain blanks from Vita Zahn Fabrik, VITA NCERAM™ ceramic blanks from Vita Zahn Fabrik, MACOR™ micaceous ceramic blanks from Corning, and DICOR™ micaceous ceramic blanks from Dentsply. A dental mill blank made of a ceramic silica material as described in U.S. Pat. No. 4,615,678. An improved ceramic dental mill blank is described in applicant's co-pending application entitled "CERAMIC DENTAL MILL BLANKS", U.S. Ser. No. 09/383,560, filed Aug. 26, 1999.

Dental mill blanks may also be made of resinous materials. An example of a dental mill blank made of a polymeric resin and a filler is described in applicant's co-pending U.S. patent application entitled "DENTAL MILL BLANKS", U.S. Ser. No. 09/227,230, filed Jan. 8, 1999. Dental mill blanks made of such material exhibit superior milling characteristics such as hardness and cutting properties relative to previously known dental mill blanks.

Many commercially available dental mill blanks are made of a two-piece construction that comprises a support stub section and a milling blank section. The support section is cylindrical and adapted to fit into a collet or a Jacobs chuck of a milling machine. Often, the support section is made of metal, since the support section is ultimately detached from the milling section and does not form part of the finished prosthetic. The support section is typically made of a relatively soft metallic material such as an aluminum alloy that is easy to machine to precise tolerances.

The milling section of conventional two-piece dental mill blank assemblies is often made of one of the aesthetically-pleasing restorative materials described above so that the resulting prosthetic provides a natural appearance once placed in the oral cavity. The milling section has a flat face that is joined to a flat face of the support section by an adhesive. An example of one type of two-piece construction is described in U.S. Pat. No. 4,615,678.

It has been observed, however, that dental mill blank assemblies occasionally fracture during the milling process. In some instances, the fracture occurs in the joint between the support stub section and the milling section. It is suspected that lateral forces exerted by the milling tool on the milling section create a shear force that exceeds the strength of the adhesive bond of the joint.

Unfortunately, if the milling section has broken away from the support section before the milling process has been completed, the mill blank assembly must be discarded and replaced with a new assembly. Consequently, the fracture of dental mill blank assemblies represents a time-wasting nuisance to the personnel operating the milling system. Replacement of the dental mill blank assembly with a new assembly also represents an additional cost to the dental laboratory, the dental practitioner and the patient that is best avoided if at all possible.

SUMMARY OF THE INVENTION

The present invention is directed toward a dental mill blank assembly that presents an enhanced resistance to fracture during the time that the mill blank assembly is machined in a milling system. The mill blank assembly is especially adapted to safely resist forces exerted by a milling tool in lateral directions so that the dental prosthetic can be milled to completion. As a result, unintentional detachment of the support section from the milling section is avoided.

In more detail, the present invention in one aspect is directed toward a mill blank assembly for a dental prosthesis, and comprises a milling section made of a material suitable for making a dental prosthesis. The mill blank assembly also comprises a support section having a shaft for releasably supporting the mill blank assembly in a milling machine. The support section is fixed to the milling section and is made of a material different than the material of the milling section. One of the milling section and the support section includes a projection, and the other of the milling section and the support section includes a recess that receives the projection.

A number of additional features are also possible. For example, the mill blank assembly may include an additional one or more projections, each of which is received in an additional, respective recess. The projections and the recesses may have closely complemental cross-sectional configurations that present a precise mating fit. Additionally, an adhesive may be provided to enhance the bond between the support section and the milling section.

Another aspect of the present invention is directed toward making a dental mill blank assembly. The method comprises the acts of providing a mold having an inlet channel and a mold cavity in communication with the inlet channel, and directing a quantity of restorative material along a path that leads through the channel and into the mold cavity. The method also includes the act of hardening restorative material located in the mold cavity as well as restorative material located in the channel. The method further includes the acts of removing the hardened restorative material from the mold cavity and the channel, and coupling the hardened restorative material to a support section. The act of coupling the hardened restorative material to a support section includes the act of inserting a portion of the hardened restorative material that was formerly in the channel into a recess of the support section.

These and other features of the invention are described in detail below and are illustrated in the accompanying drawings.

BRIEF DESCRIPTION OF THE DRAWINGS

FIG. 1 is an exploded, perspective view of a mill blank assembly for a dental prosthesis according to one embodiment of the invention, and showing a milling section and a support section as they appear before being assembled together;

FIG. 2 is a view somewhat similar to FIG. 1 but shown from a somewhat different direction;

FIG. 3 is a view somewhat similar to FIG. 2 except that the milling section and the support section have been assembled together;

FIG. 4 is an enlarged, fragmentary, side cross-sectional view of a portion of the dental mill blank assembly shown in FIG. 3;

FIG. 5 is an exploded view of a mold assembly that is especially adapted for use in making the dental mill blank assembly depicted in FIGS. 1–4; and FIG. 6 is a fragmentary perspective view of the mold assembly shown in FIG. 5, except that the mold assembly components are shown as assembled together, wherein an outer mold component has been cut away to reveal a mold cavity, and wherein a dental restorative material has been placed in the mold cavity to make the milling section of the dental mill blank assembly.

DETAILED DESCRIPTION OF THE PREFERRED EMBODIMENTS

A mill blank assembly for a dental prosthesis according to one embodiment of the invention is illustrated in FIGS. 1–4 and is broadly designated by the numeral 10. The mill blank assembly includes a stub or support section 12 and a mill blank or milling section 14 that is fixed to the support section 12.

The support section 12 includes a shaft 16 having a longitudinal axis. Preferably, the shaft 16 has an overall cylindrical shape, although other shapes are also possible. For example, the shaft 16 could have a hexagonal shape or an octagonal shape in reference planes perpendicular to its central, longitudinal axis. Preferably, an outer end of the shaft 16 is chamfered to facilitate insertion of the assembly 10 into a collet or a chuck of a milling machine.

The support section 12 also includes a flange 18 that is connected to an end of the shaft 16 that is opposite the chamfered end. The flange 18 as shown in the drawings also has a cylindrical shape, but has a diameter somewhat larger than the diameter of the shaft 16. Preferably, the central axis of the flange 18 is collinear with the central axis of the shaft 16, and presents a flat, outwardly facing bonding surface 20 having an annular configuration.

However, the flange 18 may have shapes other than cylindrical. For example, the flange 18 may have an overall square, hexagonal or octagonal shape in reference planes perpendicular to its central axis. Moreover, the central axis of the flange 18 may be laterally offset from the central axis of the shaft 16 if desired.

Preferably, the flange 18 also includes a notch 22 for receiving an indexing pin of a milling machine. As shown in the drawings, the notch 22 extends along the outer cylindrical wall of the flange 18, and extends inwardly toward the central axis of the flange. Optionally, but not necessarily, the notch 22 has a curved inner wall such that the notch 22 presents an overall, generally "U"-shaped configuration when looking in a direction along the central axis of the shaft 16.

The support section 12 may also have other features that align or enhance the coupling between the milling machine and the assembly 10. For example, the shaft 16 could have a recess or a groove that extends about its circumference to receive a setscrew or other structure of the collet or chuck. Other types of alignment or coupling-enhancing features are also possible, depending on the milling machine(s) selected.

Optionally, all or a portion of the outer cylindrical wall of the flange 18 provides a calibration surface for use during the milling process to establish tool wear. Although the calibration surface in this embodiment has the shape of a cylinder or partial cylinder, other shapes are also possible.

The calibration surface may be located next to the notch 22 or alternatively may be located on the peripheral wall in an area opposite the notch 22 relative to the central axis of the flange 18.

If a calibration surface is provided, it is preferred that the calibration surface is manufactured to be located a precise distance, within very precise dimensional tolerances, from the central axis of the flange 18. The dimensional tolerance is preferably plus or minus 0.1 mm, more preferably is plus or minus 0.05 mm and most preferably is plus or minus 0.01 mm.

The calibration surface is used by a milling machine, typically before the milling process begins, as a reference surface to accurately determine the overall dimension (such as the length) of the milling tool. As an example, the milling machine may rotate the tool while slowly moving the tool toward the calibration surface. The milling machine has a speed sensor for detecting the rotational speed of the tool and a positional sensor for tracking the axial position of the tool. The rotational speed of the tool slightly decreases as soon as the tool contacts the calibration surface. The machine is programmed to determine the overall length of the tool and compensate for tool wear by determining the axial position of the tool (i.e., the distance from the central axis of the flange 18) in relation to the calibration surface as soon as a decrease in the rotational speed is detected. Other methods to use the calibration surface as a reference surface are also possible, such as methods that employ laser sighting techniques.

The support section 12 also has a recess 24 that is located in the flange 18. In the illustrated embodiment, the recess 24 has an overall generally cylindrical shape with a central axis that is collinear with the central axis of the flange 18 and the central axis of the shaft 16. As a consequence, the recess 24 is located in this embodiment in the center of the bonding surface 20. The inner end of the recess 24 has a generally dome-shaped configuration.

However, the recess 24 may alternatively have other shapes and be located in offset relation to the central axis of the flange 18. For example, the recess 24 may have a square, rectangular, oval or other shape in reference planes perpendicular to the central axis of the flange 18. Optionally, the recess 24 may have a length sufficient to extend into the adjacent end portion of the shaft 16.

The milling section 14 includes a main body 26 as well as a projection 28 that is connected to the main body 26. Preferably, the body 26 and the projection 28 are integrally joined together and form part of a single, unitary body. In the embodiment shown in the drawings, the body 26 has an overall cylindrical shape, although other shapes are also possible.

For example, the milling section 14 may have a shape in reference planes perpendicular to its central axis that is rectangular, square, hexagonal or other types of polygons or non-polygons including oval. Preferably, but not necessarily, the central axis of the body 26 is collinear with the central axis of the projection 28. The body 26 as shown has a diameter that is smaller than the diameter of the flange 18, but as another option could have a diameter or shape larger than the diameter or shape of the flange 18 if desired.

Preferably, the projection 28 has a cross-sectional configuration in reference planes perpendicular to its central axis that is closely complemental to the cross-sectional configuration of the recess 24. As a consequence, the projection 28 matingly fits in the recess 24 when the support section 12 and the milling section 14 are assembled together.

Preferably, but not necessarily, the central axis of the body 26 and the projection 28 are collinear with the central axis of the flange 18 and the shaft 16 when the support section 12 is assembled to the milling section 14.

Preferably, the recess 24 has a length in directions along its central axis that is somewhat longer than the length of the projection 28. As a consequence, when the support section 12 is assembled to the milling section 14, the bonding surface 20 tightly contacts an annular flat bonding surface 30 of the milling section 14 that surrounds the projection 28. The extra depth provided in the recess 24 ensures that the bonding surfaces 20, 30 will fully meet even in instances where the length of the projection 28 is somewhat larger than expected.

Optionally, the cross-sectional configuration of the projection 28 is slightly larger than the cross-sectional configuration of the recess 24 in reference planes perpendicular to the central axis of the assembly 10 so that an interference fit is presented. In that instance, the projection 28 is forced under pressure into the recess 24 in order to establish a secure press-fit relationship when the support section 12 is assembled to the milling section 14.

Preferably, an adhesive is provided to enhance the bond between the support section 12 and the milling section 14. Preferably, the adhesive extends between the entire area of the bonding surfaces 20, 30, as well as along the entire cylindrical surfaces of the projection 28 and the recess 24 that are in contact with each other. The adhesive may be any suitable material that is effective in bonding the sections 12, 14 together, such as cyanoacrylate, epoxy, urethane or acrylate.

The milling section 14 is made from a material that is suitable for use in the oral cavity as a dental prosthetic and is also capable of being milled in a milling machine without undue hindrance or tool wear. Examples of suitable materials include ceramics, polymers, polymer-ceramic materials and metals.

Examples of suitable metals include stainless steel, alloys of gold or titanium, nickel-based alloys, cobalt-based alloys or any other alloy suitable for use in the oral environment. Examples of suitable alloys, palladium-based alloys, include those marketed under the tradenames Rexillium™III, Jeneric/Pentron, Inc., Wallingford, Conn.; Degudent™H, Degussa Corporation, South Plainfield, N.J.; Paladent™B, Jeneric/Pentron Inc., Wallingford, Conn.; Rexillium™ NBF, Jeneric/Pentron, Inc., Wallingford, Conn. and Allvac™-6-4, Teledyne Allvac, Monroe, N.C.

Examples of suitable ceramic materials include glasses, monocrystalline and polycrystalline ceramics, and glasses with crystalline phases. Polycrystalline ceramics include nanocrystalline materials and may be single phase or multiphase. Preferred crystalline ceramic materials include aluminum oxide, magnesium-aluminum spinel ($MgAl_2O_4$), zirconium oxide, yttrium aluminum garnet, zirconium silicate, yttrium oxide and mullite. Preferred glass containing materials include feld-pathic porcelains; glasses containing crystalline; phases such as mica, leucite, canasite, alumina, zirconia, spinel, hydroxyapatite; and amorphous glasses such as Pyrex™, Vycor™, (both from Corning, Inc., Corning, N.Y.). Preferred ceramics include those marketed under the tradenames In-Ceram™, (Vita Zahnfabnik, Bad Säckingen, Germany), Mark II™, (Vita Zahnfabnik, Bad Säckingen, Germany), ProCAD™, (Ivoclar AG, Schaan, Lichtenstein), Empress™ (Ivoclar AG, Schaan, Lichtenstein), Empress 2™ (Ivoclar AG, Schaan, Lichtenstein), MACOR™, (Coming Inc., Coming, N.Y.), DICOR™, (Dentsply International, York, Pa.), Denzir™, (Dentronic AB, Shelleftea, Sweden), Prozyr™, (Norton Desmarquest, Vincennes Cedex, France), Lucalox™, (General Electric, Richmond Heights, Ohio), Bioglass™, (U.S. Biomaterials Corp., Hachua, Fla.), Cerabone A/W, (Nippon Electric Glass, Shiga, Japan), Transtar TPA (Ceradyne, Inc., Costa Mesa, Calif.), AD-998 (Coors Ceramics, Golden, Colo.), and 998 (Vesuvius McDanel, Pa.).

The ceramic milling section may be provided either in a fully dense form, with little or no porosity, or in a porous, partially fired form. If the ceramic mill blank is porous, it may be fired to a fully dense state after milling. Alternatively, the porous ceramic mill blank may be infiltrated with, for example, a molten glass or a resin that is then hardened after infiltration.

Preferably, the ceramic material transmits light in the visible wavelengths in order to provide an aesthetically pleasing appearance once milled into a prosthetic and placed in the oral cavity. Preferably, the ceramic material is essentially colorless; i.e., it neither adds nor subtracts color to the light passing through the material to any appreciable extent. Optionally, however, colorants may be added to achieve desired shades that mimic the color of natural teeth that may be observed in certain patients.

Preferably, the ceramic mill blanks according to the invention and the resulting prosthetics have a Contrast Ratio value less than about 0.7, preferably less than about 0.6, and more preferably less than about 0.5. The Contrast Ratio value can be determined by following the technique described in Section 3.2.1 of ASTM-D2805-95, modified for samples of about 1 mm thick. The Contrast Ratio value is an indication of the level of light transmissivity possessed by the milling section 14 and the resulting prosthesis.

Further details regarding preferred ceramic dental mill blank materials and manufacturing methods for those materials, including information concerning modification of the Contrast Ratio described above, are set out in applicant's co-pending U.S. patent application entitled "CERAMIC DENTAL MILL BLANKS", U.S. Ser. No. 09/383,560, which is expressly incorporated by reference herein.

Preferred polymer-ceramic composite materials for the milling section 14 include polymerizable resins having sufficient strength, hydrolytic stability, and non-toxicity to render it suitable for use in the oral environment. Preferably, the resin is made from a material comprising a free radically curable monomer, oligomer, or polymer, or a cationically curable monomer, oligomer or polymer. Alternatively, the resin may be made from a material comprising a monomer, oligomer or polymer comprising a free radically curable functionality and a cationically curable functionality. Suitable resins include epoxies, methacrylates, acrylates and vinyl ethers.

Polymers for the polymer-ceramic composite milling section 14 include thermoplastic and thermosetting polymers. Suitable thermoplastic polymers include polycarbonates, nylon, polyetheretherkitone, polyurethanes, polyimides and polyamides. The polymer material may be filled with one or more types of ceramic filler as described below.

The polymer-ceramic composite material also includes an initiator for initiating polymerization of the material. For example, one class of useful initiators includes those capable of initiating both free radical and cationic polymerization. Preferred free radical polymerization systems contain three components: an onium salt, a sensitizer and a free radical donor. Optionally, the sensitizer may be a visible light sensitizer that is capable of absorbing light having wavelengths in the range from about 3 nanometers to about 1000 nanometers. If the resin in the polymer-ceramic composite is not sufficiently hardened before milling, further hardening can be carried out after milling and before use in the oral cavity.

Preferably, the polymer-ceramic composite material also includes a filler. The filler is preferably a finely divided material that may optionally have an organic coating. Suitable coatings include silane or encapsulation in a polymeric matrix. The filler may be selected from one or more of many materials suitable for incorporation in compositions used for medical or dental applications, such as fillers currently used in dental restorative compositions and the like.

Suitable fillers include zirconia-silica, baria-silica glass, silica, quartz, colloidalsilica, fumed silica, ceramic fibers, ceramic whiskers, calcium phosphate, fluoroaluminosilicate glass and rare-earth fluorides. Suitable fillers also include nanosize heavy metal oxide particles such as described in applicant's co-pending patent application entitled "RADIOPAQUE DENTAL MATERIALS WITH NANO-SIZED PARTICLES"; U.S. Ser. No. 09/429,185 filed Oct. 28, 1999, which is expressly incorporated by reference herein. Other suitable fillers are described in applicant's co-pending patent applications entitled "CLUSTERED PARTICLE DENTAL FILLERS" (U.S. Ser. No. 09/428,830 filed Oct. 28, 1999) and "DENTAL MATERIALS WITH NANO-SIZED SILICA PARTICLES" (U.S. Ser. No. 09/428,937 filed Oct. 28, 1999), both of which are expressly incorporated by reference herein. Additional suitable fillers are described in U.S. Pat. No. 4,503,169, and applicant's co-pending patent application entitled "RADIOPAQUE CATIONICALLY POLYMERIZABLE COMPOSITINS COMPRISING A RADIOPAQUE FILLER, AND METHOD FOR POLYMERIZING SAME" (U.S. Ser. No. 09/168,051 filed Oct. 7, 1998), both of which are incorporated by reference herein. The fillers may be in any morphology, including spheres, platelets, whiskers, needles, fibers, ovoids, etc. or any combination of the foregoing.

Further information regarding preferred polymer-ceramic composite materials, including details of suitable compositions and method of manufacturing those materials, are set out in applicant's co-pending U.S. patent application entitled "DENTAL MILL BLANKS", U.S. Ser. No. 09/227,230, which is also expressly incorporated by reference herein.

The milling section 14 is suitable for fabricating into a variety of restorations, including inlays, onlays, crowns, veneers, bridges, implant abutments, copings and bridge frameworks. Various means of machining the milling section 14 may be employed to create custom-fit dental prosthesis having a desired shape. It is preferable that the prosthesis be milled quickly without imparting undue damage. Preferably, the prosthesis is milled by computer controlled milling equipment, such as machines sold under the tradenames Sirona CEREC 2, Sirona CERAC 3, Dentronics DECIM or CadCam Ventures PROCAM.

By using a CAD/CAM milling device, the prosthesis can be fabricated efficiently and with precision. During milling, the contact area may be dry, or it may be flushed with or immersed in a lubricant. Alternatively, it may be flushed with an air or gas stream. Suitable liquid lubricants are well known, and include water, oils, glycerine, ethylene glycols, and silicones. After milling, some degree of finishing, polishing and adjustment may be necessary to obtain a custom fit in to the mouth and/or aesthetic appearance.

The support section 12 is made of a material that can be manufactured to relatively precise tolerances and has sufficient strength for supporting the assembly in a collet or chuck of a milling machine. An example of a suitable material is aluminum. Optionally, the aluminum may be plated with gold chromate in order to enhance the bond between the support section 12 and the adhesive.

As another option, the support section 12 may be made of an aluminum which has been anodized. It has been found that an anodized surface is very effective in enhancing the bond between the support section 12 and the adhesive. A black anodized surface is presently preferred.

One method of making the mill blank assembly 10 shown in FIGS. 1–4 is illustrated in FIGS. 5 and 6. In FIGS. 5 and 6, a mold or mold assembly 36 includes a male first or inner component 38 and a female second or outer component 40. Optionally, the first and second components 38, 40 are made of a relatively inexpensive material such as injection-molded plastics. Suitable materials for the components 38,40 include acrylics (such as polymethylmethacryate ("PMMA")), polycarbonates, polystyrene and polyethylene terephthalate ("PET"). The components 38, 40 are preferably discarded after a single use to make the milling section 14.

The first mold component 38 includes a plunger portion 42 as well as a rear portion 44. The second mold component 40 is hollow and presents a front portion 46 and a rear portion 48. The plunger portion 42 of the first component 38 and the front portion 46 of the second component 40 have matching circular shapes when viewed in reference planes perpendicular to a central axis of the mold assembly 36. The rear portion 44 of the first component 38 and the rear portion 48 of the second component 40 have matching, but somewhat larger circular shapes when viewed in references planes perpendicular to the central axis of the mold assembly 36. (The relative shapes for the portions 42, 44 and the portions 46, 48 are optional and may be varied according to the desired diameter of the milling section 14. For example, the portions 42, 44 and the portions 46, 48 could have identical cross-sections.)

When the first component 38 is received in the second component 40, the plunger portion 42 slides in the front portion 46 while the rear portion 44 slides within the rear portion 48. Preferably, the matching circular shapes of the portions 42, 46 and the matching circular shapes of the portions 44, 48 present a close mating fit so that the first component 38 smoothly slides within the second component 40 without undue lateral movement or "slop".

As shown in FIG. 5, the second component 40 also includes a cylindrical channel 50 that is located in the center of the front portion 46. The channel 50 leads to an internal mold cavity 52 that is located between a front face of the plunger portion 42 and a front inner wall of the front portion 46 when the components 38, 40 are assembled together. The channel 50 provides an inlet opening for the introduction of restorative material into the mold cavity 52 when it is desired to make a milling section such as the milling section 14 described above.

In use, the components 38, 40 are fully assembled such that the front face of the plunger 42 initially is closely adjacent, and preferably is in contact with the front wall of the front portion 46. In this orientation of the components 38, 40, the volume of space in the mold cavity is essentially zero. Next, a quantity of flowable, unhardened dental restorative material is introduced into the channel 50 and into the mold cavity 52. As the restorative material is introduced into the mold cavity 52, the restorative material pushes against the front face of the plunger portion 42 and the front, inner wall of the first portion 46. The force exerted by the incoming restorative material pushes the components 38, 40 away from each other. If, for example, the second component 40 is held stationary, the first component 38 moves in a rearwardly direction in the second component 40.

As the mold cavity 52 is filled, the flowing restorative material continues to bear against the front face of the plunger portion 42, thereby helping to ensure that air bubbles are not created in the mass of restorative material in the mold cavity 52 as the mold cavity 52 enlarges in volume. Avoidance of air bubbles in the restorative material is desired so that the resulting milling section is strong and does not present voids that might otherwise appear within or on the surface of the resulting prosthetic.

Preferably, back pressure is applied to one or both of the components 38, 40 as the mold cavity 52 is filled. If, for example, the second component 40 is held stationary as mentioned above while the mold cavity 52 is filled, pressure is applied to the first component 38 so that the first component 38 does not freely move away from the second component 40. The back pressure can be applied by use of a piston (of a hydraulic piston and cylinder assembly) in contact with the outer face of the rear portion 44. Preferably, the amount of pressure applied to the first component 38 is slightly less than the pumping pressure (i.e., the amount of pressure that is applied to the restorative material in order to cause the restorative material to flow into the mold cavity 52). In this manner, the likelihood of air bubbles in the resulting milling section is reduced.

In FIG. 6, the restorative material is designated by the numeral 54. FIG. 6 also shows an example of the position of the first component 38 relative to the second component 40 after a sufficient amount of restorative material has been introduced into the mold cavity 52 to make a milling section. The restorative material in the mold cavity 52 and also in the channel 54 is then hardened to present a unitary body that is suitable for use as a milling section, such as the milling section 14 described above.

When the restorative material 54 is a polymer-ceramic composite material as described above and includes a visible light sensitizer, the restorative material 54 is hardened by directing a source of light toward the mold cavity 52. For this purpose, the second component 40 and preferably both of the first and second components 38, 40 are made of a transparent or translucent material that is capable of transmitting actinic radiation. Once the restorative material 54 has sufficiently hardened, the first component 38 is removed from the second component 40 and the resulting milling section is removed from the mold cavity 52 and the channel 50.

The portion of the hardened restorative material 54 that was previously in the channel 50 presents a projection such as the projection 28 described above. As a consequence, there is no need to remove the projection after the molding operation is complete, as might otherwise be desired to present a flat face for bonding to a flat face of a support section as known in the prior art. Such a method also avoids the need for attempting to remove material from the channel 50 before hardening the material in the mold cavity 52.

The projection 28 is also an advantage during coupling of the support section 12 to the milling section 14, in that the projection 28 serves to align the sections 12, 14 to a desired orientation. For example, and in the embodiment described above, if the projection 28 and the recess 24 each have a central axis that is collinear with a central axis of the assembly 10, the milling section 14 will be in its desired alignment to the support section 12 when the two sections 12, 14 are brought together for bonding. In this manner, the likelihood of lateral misplacement of one of the sections 12, 14 relative to the other during assembly of the sections 12, 14 is reduced.

Once the sections 12, 14 are assembled together, the projection 28 functions as a support structure to resist lateral shear forces. For example, if a lateral force is applied by a milling tool against the milling section 14, the projection 28 (in combination with the adhesive) helps the assembly 10 in resisting the force so that the milling section 14 will remain securely fixed to the support section 12 during the remainder of the milling process (until such time in the process that detachment of the support section 12 is desired).

As an additional option, the projection 28 and the recess 24 may be provided with mating keys and keyways or other structure in order to ensure that the support section 12 is in a desired rotational position (i.e., in directions about the central axis of the assembly 10) relative to the rotational position of the milling section 14. For example, if the milling section 14 has a somewhat square configuration in transverse cross-section, it may be preferred to align one side of the square to the position of the notch 22 located on the support section 12. In this manner, the square configuration of the milling section will be oriented in a certain position relative to the milling machine as may be desired, for example, in order to optimize use of the milling section 14.

As another option, one or more additional projections may be provided. If a plurality of projections are provided, the projections may be symmetrical with respect to the central axis of the assembly 10 or alternatively may be non-symmetrical in order to provide rotational alignment of the sections 12, 14 as described above. As a further option, the projection or projections could extend from the support section and into respective recesses of the milling section. Moreover, projections could extend from both the support section and the milling section into recesses of the other.

The projection 28 may also have shapes other than that shown in the drawings. For example, the projections may be in the form of fibers, a machined surface, a mesh surface, a roughened surface or an irregular surface (such as, for example, may be presented by upstanding shards of hardened restorative material). As an additional option, the projections may include pores or recesses for bond enhancement. Furthermore, the projection(s) could have a longitudinal axis that extends perpendicular to the central axis of the assembly, such as one or more projections in the shape of cross bars that extend across all or a portion of the diameter of the bonding surface 20.

The method of making the milling section 14 may also vary from that shown in FIGS. 5 and 6. For example, the channel 50 could be eliminated if desired and one or more recesses could be provided in the front face of the plunger portion 42 in order to provide space for the restorative material to form one or more projections. The restorative material may also be introduced through a channel in the first mold component 38 that optionally is the same or in communication with the recess mentioned in the preceding paragraph. Furthermore, the projection or projections could be milled or otherwise machined into the milling section after the restorative material is hardened.

A variety of other constructions and methods are also possible and may be apparent to those skilled in the art. As such, the scope of the invention should not be deemed limited to the presently preferred embodiments that are described in detail above, but instead only by a fair scope of the claims that follow along with their equivalents.

What is claimed is:

1. A method of making a dental mill blank assembly comprising the acts of:
    providing a mold having an inlet channel and a mold cavity in communication with the inlet channel;
    directing a quantity of restorative material along a path that leads through the channel and into the mold cavity;
    hardening restorative material located in the mold cavity as well as restorative material located in the channel;
    removing the hardened restorative material from the mold cavity and the channel; and
    coupling the hardened restorative material to a support section, wherein the act of coupling the hardened restorative material to a support section includes the act of inserting the portion of the hardened restorative material that was formerly in the channel into a recess of the support section.

2. A method of making a dental mill blank assembly according to claim 1 and including the act of providing a quantity of adhesive between the hardened restorative material and the support section.

3. A method of making a dental mill blank assembly according to claim 1 wherein the act of inserting the portion of the hardened restorative material that was formerly in the channel into a recess of the support section is carried out by sliding the portion of the hardened restorative material into the recess in mating, complemental relation.

4. A method of making a dental mill blank assembly according to claim 1 wherein the act of providing a mold having an inlet channel and a mold cavity in communication with the inlet channel includes the act of locating a central axis of the inlet channel in alignment with a central axis of the mold cavity.

5. A method of making a mill blank assembly according to claim 1 wherein the act of hardening restorative material located in the mold cavity as well as restorative material located in the channel is carried out by directing a source of light toward the mold cavity.

6. A method of making a dental mill blank assembly comprising the acts of:
    providing a mold assembly having a first component, a second component and a mold cavity located between a front face of tile first component and an inner wall of the second component;
    moving the first component and the second component relative to each other such that the front face of the first component is adjacent the inner wall of the second component;
    directing a quantity of restorative material alone a path that leads through a channel in communication with the mold cavity and to a location between the front face of the first component and the inner wall of the second component;
    introducing the restorative material into the mold cavity under pressure such that the restorative material bears against the front face of the first component and the inner wall of the second component and relatively moves the front face and the inner wall away from each other;
    hardening restorative material located in the mold cavity as well as restorative material located in the channel; and
    coupling the hardened restorative material to a support section, wherein the act of coupling the hardened restorative material to a support section includes the act of inserting the portion of the hardened restorative material that was formerly in the channel into a recess of the support section.

7. A method of making a dental mill blank assembly according to claim 6 wherein the act of moving the first component and the second component relative to each other such that the front face of the first component is adjacent the inner wall of the second component includes the act of contacting the front face with the inner wall.

8. A method of making a dental mill blank assembly according to claim 6 and including the act of hardening restorative material located in the mold cavity to make a milling section.

9. A method of making a dental mill blank assembly according to claim 8 wherein the act of hardening restorative material in the mold cavity to make a milling section includes the act of directing a source of light toward the mold cavity.

10. A method of making a dental mill blank assembly according to claim 8 and including the act of assembling the milling section to a support section.

11. A method of making a dental mill blank assembly according to claim 6 and including the act of applying pressure to at least one of the mold components during at least a portion of the time that restorative material is introduced into the mold cavity in order to resist free movement of the mold components in directions away from each other.

12. A method of making a dental mill blank assembly according to claim 6 wherein the act of moving the first component and the second component relative to each other includes the act of slidably moving the first component and the second component relative to each other.

13. A method of making a dental mill blank assembly according to claim 6 wherein the act of moving the first component and the second component relative to each other includes the act of moving the first component and the second component in telescoping relationship.

14. A method of making a dental mill blank assembly according to claim 6 wherein the act of moving the first component and the second component relative to each other includes the act of holding the second component in a stationary position while moving the first component into the second component.

15. A method of making a dental mill blank assembly according to claim 6 and including the act of providing a quantity of adhesive between the hardened restorative material and the support section.

* * * * *

UNITED STATES PATENT AND TRADEMARK OFFICE
CERTIFICATE OF CORRECTION

PATENT NO.     : 6,482,284 B1
DATED          : November 19, 2002
INVENTOR(S)    : Reidt, Dean K. et al.

It is certified that error appears in the above-identified patent and that said Letters Patent is hereby corrected as shown below:

Column 7,
Line 67, delete "Coming" and insert in place thereof -- Corning --.

Column 13,
Line 43, delete "tile" and insert in place thereof -- the --.
Line 48, delete "alone" and insert in place thereof -- along --.

Signed and Sealed this

First Day of July, 2003

JAMES E. ROGAN
*Director of the United States Patent and Trademark Office*